United States Patent [19]

Knutsson

[11] Patent Number: 4,929,466

[45] Date of Patent: May 29, 1990

[54] FOOD AND FEEDSTUFF

[75] Inventor: Maud I. C. Knutsson, Vagnhärad, Sweden

[73] Assignee: Ewos Aktiebolag, Sodertalje, Sweden

[21] Appl. No.: 190,269

[22] Filed: May 3, 1988

[30] Foreign Application Priority Data

May 5, 1987 [SE] Sweden ............................... 8701839

[51] Int. Cl.$^5$ ................................................ A23K 1/17
[52] U.S. Cl. .................................... 426/615; 426/634; 426/635; 426/637; 426/641
[58] Field of Search ................ 426/53, 54, 2, 635, 426/615, 627, 634, 637, 641

[56] References Cited

U.S. PATENT DOCUMENTS

| | | | |
|---|---|---|---|
| 3,950,543 | 4/1976 | Buffa et al. | 426/53 |
| 4,320,116 | 3/1982 | Björck | 424/130 |
| 4,413,018 | 11/1983 | Webster | 426/618 |
| 4,438,100 | 3/1984 | Balslev et al. | 424/104 |
| 4,450,176 | 5/1984 | Stahel | 426/2 |
| 4,544,564 | 10/1985 | Bookwalter . | |
| 4,617,190 | 10/1986 | Montgomery . | |
| 4,726,948 | 2/1988 | Pricels et al. | 426/648 |

FOREIGN PATENT DOCUMENTS 0200565 2/1986 European Pat. Off. .

*Primary Examiner*—Donald E. Czaja
*Assistant Examiner*—D. Workman
*Attorney, Agent, or Firm*—Brumbaugh, Graves, Donohue & Raymond

[57] ABSTRACT

The present invention relates to a food and feedstuff intended to be able to function in connection with an antibacterial system comprising lactoperoxidase-thiocyanate-hydrogen peroxide donor, and salivary peroxide-thiocyanate-hydrogen peroxide donor, respectively, whereby the vegetables present in the food and the feedstuff have been treated in such a way that vegetable peroxidases present have become deactivated.

15 Claims, No Drawings

FOOD AND FEEDSTUFF

DESCRIPTION

1. Technical Field

The present invention relates to a food, such as in the form of soya milk, milk replacer, and feedstuff for animals, particularly a feedstuff for young animals, such as calves, pigs, dogs, cats, chicken, and others, and intended to able to function together with an antibacterial system in the form of lactoperoxidase-thiocyanate-hydrogen peroxide donor, (the LP-system), and salivary peroxides-thiocyanate-hydrogen peroxide donor (the SP-system).

The object of the present invention is to obtain a food and a feedstuff based substantially on vegetables, in which food and/or feedstuff the so called LP-system or the SP-system can function completely.

2. Background of the Invention

It is previously known and described an antibacterial system called the LP-system, which comprises the enzyme lactoperoxidase, a thiocyanate, and a hydrogen peroxide donor, the latter either in the form of a hydrogen peroxide donating enzymatic system (glucose/-glucoseoxidase, xanthine/xanthineoxidase) or in the form of a solid peroxide (sodium percarbonate, magnesium peroxide, carbamide peroxide), a solid peroxid system (Cu+ascorbic acid) or added with Lactobacillae producing hydrogen peroxide. The system has shown to possess a good antibacterial effect and has also turned out to function well under anaerobic conditions (when solid peroxides are used), such as in the gastro-intestinal tract. One has thereby been able to prevent diarrhoea in young animals. These types of diarrhoea are often present in animal stocks, and particularly among piglets, where this form of diarrhoea kills many animals, and/or reduces the growth rate, which factors are of great economical value. The use of the LP-system is also of utmost interest as antibiotics in the form of penicillins and tetracyclines thereby can be used to a less extent; products which have been highly critisised due to the risk of rise of resistancy, and risk of residues of the compound in the slaugthered meat. Saliva peroxidase is ranked with lactoperoxidase in this respect, and below when using the LP-system it shall be understood that one can use salivary peroxidase in stead.

It has, however, turned out that the LP-system has not always had the expected effect, when it has been added to vegetable based feedstuffs, such as feedstuffs comprising cereals, peas, soya, potatoes, and beet pulp. After investigations and research made one has surprisingly found that the peroxidases present in these products very efficiently compete with lactoperoxidase, as they have a greater affinity to hydrogen peroxide than the lactoperoxidase enzyme has.

It is surprising to find that the antibacterial system is outbeaten by vegetable peroxidases as one has been of the opinion that LP has a very high affinity to hydrogen peroxide which exceeds that of other enzymes. E.g., catalase has not been able to compete with LP within the levels present, as far as one knows hitherto.

It is known, and possible to buy, a soya meal on the market which has been heavily heat treated in order to decompose tryptinase, a trypsine inhibitor, and generally all soya meal is tested for the presence of urease to show the presence or not of trypsine inhibitor, as urease is decomposed simultaneously. However, it has turned out that this heavy heat treatment of the soya meal does not destroy the vegetable peroxidases present.

One object of the present invention is, as mentioned above, thus to obtain a food and feedstuff, particularly feedstuff for young animals in which the LP-system can be active and have an effect all way out.

An additional object is thereby to obtain a digestible, pregelatinized starch present in such vegetables as such gelatinized starch is more easily digested by the young stomach.

DESCRIPTION OF THE PRESENT INVENTION

It has now surprisingly been found possible to meet this request and to obtain a food and a feedstuff based on vegetables in which the LP-system can be activated and/or be brought into action endogenously, whereby the invention is characterized in that the ingoing vegetables are pretreated in such a way that vegetable peroxidase present is deactivated.

The term vegetable peroxidase means all such peroxidases which have a greater affinity to hydrogen peroxide than lactoperoxidase and/or salivary peroxidase.

The invention is particularly characterized in that ingoing vegetables are heated to 100° C. to 175° C. in the presence of a certain critical amount of moisture, which means mainly a 100% relative humidity and derived from free, unbound water present in the material. So called hydrothermic processes function best, e.g., "cooking extrusion", or autoclaving, alternatively. At extrusion a moist, paste shaped material is pressed under a high pressure through a matrix whereby due to the frictional heat, the temperature increases considerably to the above given temperatures in the material and simultaneously as the water present boils.

Microwave heating and micronization takes place at a high temperature as well but in a relatively dry condition. As evident from the table below micro wave heating and micronization do not give a complete elimination of vegetable peroxidases.

Ingoing amino acids, particularly lysine, arginine, and cystine, may not, on the other hand, be subject to such high temperatures that a considerable decomposition or other unwanted reactions (e.g. Maillard reactions) occur, such as the formation of —SH groups which block the bactericidal effect by competetion for —OSCN−. Vegetable components should thus be heat treated per se, and the animalic components be treated per se, and then be mixed together in dry state.

Further characteristics are evident from the accompanying claims.

The invention will be described in the following with reference to a number of examples, however, without being restricted thereto.

The peroxidase activity has been determined for a great number of vegetables by means of a method using guajakol, which reacts with most peroxidases.

The result is evident from Table 1 below. In the table peroxidase activity is expressed in the following way:

TABLE 1

| Product | Treatment | Activity |
|---|---|---|
| Wheat | untreated | +++ |
| Wheat | scalded | +++ |
| Wheat | ac 20 min | − |
| Wheat | micro waves 4 min | +++ |
| Wheat | extruded | − |
| Corn | untreated | ++ |
| Corn | micronization | + |
| Corn | ac 120° C., 20 min | − |
| Popcorn, ground | untreated | ++ |

TABLE 1-continued

| Product | Treatment | Activity |
|---|---|---|
| Popcorn, ground | popped in oil | — |
| Barley | untreated | +++ |
| Barley | scalded | +++ |
| Barley | ac 120° C., 20 min | — |
| Barley | micronization | +++ |
| Green peas | untreated | +++ |
| Green peas | ac 120° C., 20 min | — |
| Yellow peas | untreated | +++ |
| Yellow peas | ac 120° C., 20 min | — |
| Peas | micronization | +++ |
| Beet cuttings | untreated | + |
| Soya, ground | untreated | +++ |
| Soya, ground | 125° C., 30 min | ++ |
| Soya, ground | 150° C., 15 min | ++ |
| Soya, ground | 150° C., 30 min | + |
| Soya, ground | micronization | +++ |
| Soya, ground | 150° C., 45 min | — |
| Soya, ground | 175° C., 15 min | — |
| Soya, ground | ac 120° C., 20 min | — |
| Soya protein conc. | untreated | — |
| Rapeseed | untreated | — |
| Soya milk | untreated | ++ |
| Soya milk | boiled 15 min | — |
| Soya milk | ac 120° C., 20 min | — |
| Soya milk | ac 1 atm, 15 min | — |
| Potatoes | untreated | +++ |
| Potatoes | boiled | — |
| Pig fodder I | untreated | +++ |
| Pig fodder I | 150° C., 15 min | ++ |
| Pig fodder I | 175° C., 15 min | — |
| Pig fodder I | ac 120° C., 20 min | — |
| Pig fodder II | untreated | +++ |
| Pig fodder II | 125° C., 15 min | + |
| Pig fodder II | 150° C., 15 min | — |
| Pig fodder II | ac 120° C., 20 min | — |
| Pig fodder III | untreated | +++ |
| Animal fodder IV | untreated | +++ |
| Animal fodder IV | ac 120° C., 20 min | — |
| Animal fodder V | untreated | +++ |
| Animal fodder VI | untreated | +++ |
| Animal fodder VII | untreated | ++ |
| Piglet fodder base | extruded | — | ac = autoclaved
+++ = very high activity;
++ = high acitivity
+ = activity
— = no activity Pig fodder I—Animal fodder VII are different feedstuffs present on the market, preferably produced for piglet and young pig production.

As evident from the Table above a considerable heat treatment is needed to eliminate the vegetable peroxidase activity.

The following feedstuffs have been tested:

| Fodder A | Skim milk powder | 1 g |
|---|---|---|
| | Lactose reduced whey powder | 0.5 g |
| | Fish meal | 1 g |
| | Extruded piglet fodder base | 7.0 g |
| | Potatoe starch | 0.2 g |
| | Vitamins & minerals mix | 0.3 g |
| | Aq. dest sterile | 40 ml |
| Fodder B | Vitamins & minerals mix | 2.2% |
| | Skim milk powder | 10.0% |
| | Lactose reduced whey powder | 5.0% |
| | Potatoe starch | 2.0% |
| | Fish meal | 10.0% |
| | Baker's yeast | 1.0% |
| | Piglet fodder base* | 69.8% |
| Fodder C = Pig fodder III in Table 1 above. | | |
| Fodder D = Animal fodder VII in Table 1 above. | | |
| Fodder E | Vitamins & Minerals mix | 2.1% |
| | Lactose reduced whey powder | 15.0% |
| | Fish meal | 11.5% |
| | Extruded cereals + fat | 71.4% |
| Piglet fodder base | Soya meal | 13% |
| | Potatoe fibre | 3% |
| | Fat - cooking oil | 4% |
| | Wheat meal | 80% |

*crude, and extruded, respectively

The tests were made using the following method: The feedstuff was mixed dry or is weighed and mixed with water, optionally comprising lactoperoxidase. Then the pH is adjusted using 1M HCL and 5 ml sample is brought to a testing tube using a pipette. Other ingredients are added according to scheme, and the test organism, E. coli NCTC 9703 is added. A control sample is taken out, diluted in peptone water and transferred onto a MacConkey-agar plate. The samples are incubated at 37° C. on a water bath. After 2 hrs a final sample is taken to check the number of remaining cfu/ml in the sample, is diluted with peptone water, and is transferred onto a MacCokney agar plate. The agar plates are incubated at 37° C. in a heating cabinet and are read after 24 hrs. The results of the tests are given in Table 2 below. In certain tests cysteine-HCl has been added which amino acid is known to inhibit the LP-system.

As evident from Table 2 inhibition of the LP-system takes place, besides in those cases when cystein is present, in these cases when ++ or +++ activity is present in the basic fodder, while when — activity is at hand the LP-system functions and gives a killing of the test micro organism added. In all cases the dry substance contents of the feedstuff mixtures have been adjusted to about 20–25%, which corresponds to a dilution factor of 1+3, and 1+4, respectively, i.e., 1 part of dry feeding stuff + 3–4 parts of water.

TABLE 2

| Testmedium | pH | LP μg/ml | NaSCN mM | MgO₂ mg/ml | Cyst-HCl mM | 0 hrs log-cfu/ml | 2 hrs log-cfu/ml |
|---|---|---|---|---|---|---|---|
| Fodder A (—) activity | 5,5 | | | | | 7,26 | 8,04 |
| | 5,5 | 10 | 1 | 0,3 | | 7,11 | 4,65 |
| | 5,5 | 10 | 1 | 0,3 | 4 | 7,04 | 8,08 |
| Fodder A (—) activity | 5,5 | | | | | 6,72 | 7,88 |
| | 5,5 | 10 | 1 | 0,3 | | 6,57 | <3,00 |
| | 5,5 | 10 | 1 | 0,3 | 4 | 6,81 | 8,15 |
| Fodder B (—) activity | 5,5 | | | | | 6,92 | 7,41 |
| | 5,5 | 10 | | | | 6,38 | <3,00 |
| Fodder B (—) activity | 5,5 | 10 | | | | 6,87 | 8,11 |
| | 5,5 | 10 | 1 | 0,3 | | 6,67 | 3,00 |
| | 5,5 | 10 | 1 | 0,3 | 4 | 6,93 | 8,00 |
| Fodder B (+++) activity | 5,5 | 10 | | | | 7,04 | 8,18 |
| | 5,5 | 10 | 1 | 0,3 | | 7,00 | 8,18 |
| | 5,5 | 10 | 1 | 0,3 | 4 | 6,98 | 8,30 |
| Fodder B (—) activity | 5,5 | 10 | | | | 6,79 | 8,04 |
| | 5,5 | 10 | 1 | 0,3 | | 7,18 | 3,26 |
| | 5,5 | 10 | 1 | 0,3 | 4 | 7,08 | 8,30 |

TABLE 2-continued

| Testmedium | pH | LP μg/ml | NaSCN mM | MgO2 mg/ml | Cyst-HCl mM | 0 hrs log-cfu/ml | 2 hrs log-cfu/ml |
|---|---|---|---|---|---|---|---|
| Fodder B (−) activity | 5,5 | 10 | | | | 6,64 | 5,63 |
| | 5,5 | 10 | 1 | 0,3 | | 6,32 | 3,57 |
| | 5,5 | 10 | 1 | 0,3 | 4 | 6,76 | 8,18 |
| Fodder C (+++) activity | 5,2 | | | | | 6,74 | 6,83 |
| | 5,2 | 10 | 1 | 0,3 | | 6,76 | 6,20 |
| | 5,2 | 10 | 1 | 0,3 | 4 | 6,74 | 7,38 |
| Fodder D (++) activity | 5,0 | | | | | 6,65 | 6,59 |
| | 5,0 | 10 | 1 | 0,3 | | 6,72 | 6,20 |
| | 5,0 | 10 | 1 | 0,3 | 4 | 6,69 | 6,66 |
| Fodder E (+++) activity | 5,5 | 10 | | | | 6,74 | 6,75 |
| | 5,5 | 10 | 1 | 0,3 | | 7,03 | 5,26 |
| | 5,5 | 10 | 1 | 0,3 | 4 | 7,18 | 7,60 |
| Fodder E (++) activity | 5,5 | 10 | | | | 6,65 | 5,89 |
| | 5,5 | 10 | 1 | 0,3 | | 6,65 | <2,00 |
| | 5,5 | 10 | 1 | 0,3 | 4 | 6,76 | 7,59 |
| Soya milk (++) activity | 5,5 | 10 | 1 | 0,3 | | 6,74 | 5,08 |
| | 5,5 | 10 | 1 | 0,3 | 4 | 6,72 | 8,11 |
| Soya milk (−) activity | 5,5 | 10 | 1 | 0,3 | | 6,72 | 2,36 |
| | 5,5 | 10 | 1 | 0,3 | 4 | 6,60 | 7,66 |
| Soya milk (−) activity | 5,5 | 10 | 1 | 0,3 | | 6,73 | 2,36 |
| | 5,5 | 10 | 1 | 0,3 | 4 | 6,73 | 7,46 |

Fodder E (+++) activity had a high content of vegetable peroxidase due to failed extrusion
Fodder E (++) activity is the same fodder as that with (+++) activity, but here the vegetable peroxidases have been eliminated. (++) activity depends on the addition of 15% of lactose reduced whey which gives a mark in the guajakol test, due to lactoperoxidase.

I claim:

1. A feedstuff comprising vegetable matter from rootcrops in combination with an antibacterial system, the antibacterial system being selected from the group consisting of a lactoperoxidase thiocyanate-hydrogen peroxide donor and a salivary peroxidase-thiocyanate-hydrogen peroxide donor, wherein the vegetable peroxidases present in the vegetable matter have been deactivated by boiling the vegetable matter for at least 15 minutes.

2. A method for the preparation of a feedstuff comprising vegetable matter in combination with an antibacterial system, the antibacterial system being selected from the group consisting of a lactoperoxidase-thiocyanate hydrogen peroxide donor and a salivary peroxidase-thiocynate-hydrogen peroxide donor, comprising deactivating the vegetable peroxidases present in the vegetable matter by heat treating the vegetable matter for at least 15 minutes and combining said deactivated vegetable matter with said antibacterial system.

3. The method according to claim 2 wherein the vegetable matter is heat treated in the presence of moisture at a temperature between 100° to 175° C. and a relative humidity of about 100% so as to inactivate said vegetable peroxidases.

4. The method according to claim 3 wherein said vegetable matter is selected from the group consisting of cereals, legumes and soya.

5. The method according to claim 3 wherein said vegetable matter comprises root crops and boiling said root crops for at least fifteen minutes.

6. A feedstuff comprising vegetable matter in combination with an antibacterial system, the antibacterial system being chosen from the group consisting of a lactoperoxidase-thiocyanate-hydrogen peroxide donor and a salivary peroxidase-thiocyanate-hydrogen peroxide donor, wherein the vegetable peroxidases present in the vegetable matter have been deactivated by heat treating such vegetable matter at at least 120° C. at a relative humidity of about 100% for at least 15 minutes.

7. The feedstuff according to claim 6, wherein said vegetable matter is chosen from the group consisting of cereals, legumes and soya.

8. The feedstuff according to claim 6, wherein said vegetable matter comprises soya which has been heat treated at a temperature of at least 150° C. for fifteen to seventy-five minutes.

9. A method for the preparation of a feedstuff containing vegetable matter in combination with an antibacterial system, comprising deactivating the vegetable peroxidases present in the vegetable matter by heat treating said vegetable matter in the presence of moisture at a temperature of at least 120° C. and a relative humidity of about 100% for at least fifteen minutes, and combining said treated vegetable matter with said antibacterial system.

10. The method according to claim 9, wherein said vegetable matter is autoclaved at approximately 120° C.

11. The method according to claim 9, wherein said vegetable matter is selected from the group consisting of cereals, legumes and soya.

12. The method according to claim 9, wherein said vegetable matter comprises soya, and said soya is heat treated at a temperature of at least 150° C. for fifteen to seventy-five minutes.

13. A method for the preparation of feedstuff comprising vegetable matter in combination with an antibacterial system, the antibacterial system being selected from the group consisting of a lactoperoxidase-thiocyanate-hydrogen peroxide donor and a salivary-peroxidase-thiocyanate hydrogen peroxide donor, comprising deactivating the vegetable peroxidases present in the vegetable matter by cooking extrusion of the vegetable matter and combining said deactivated vegetable matter with said antibacterial system.

14. A feedstuff comprising vegetable matter in combination with an antibacterial system, the antibacterial system being selected from the group consisting of lactoperoxidase-thiocyanate-hydrogen peroxide donor and a salivary peroxidase-thiocyanate-hydrogen peroxide donor, wherein the vegetable peroxidases present in the vegetable matter have been deactivated by heat treating the vegetable matter for at least 15 minutes.

15. A feedstuff comprising vegetable matter in combination with an antibacterial system, the antibacterial system being selected from the group consisting of lactoperoxidase-thiocyanate-hydrogen peroxide donor and a salivary peroxidase-thiocyanate-hydrogen peroxide donor, wherein the vegetable peroxidases present in the vegetable matter have been deactivated by cooking extrusion of the vegetable matter.

* * * * *

UNITED STATES PATENT AND TRADEMARK OFFICE
CERTIFICATE OF CORRECTION

PATENT NO. : 4,929,466

DATED : May 29, 1990

INVENTOR(S) : Knutsson

It is certified that error appears in the above-identified patent and that said Letters Patent is hereby corrected as shown below:

<u>Col. 1, line 10</u>, "to" should read --to be--;

<u>Col. 1, line 13</u>, "peroxides-" should read --peroxidase- --;

<u>Col. 1, line 27</u>, "peroxid" should read --peroxide--;

<u>Col. 1, line 42</u>, "critisied" should read --criticized--;

<u>Col. 1, line 44</u>, "slaugthered" should read --slaughtered--;

<u>Col. 1, line 44</u>, "Saliva" should read --Salivary--;

<u>Col. 2, line 45</u>, "competetion" should read --competition--;

<u>Col. 4, line 36</u>, "MacCokney" should read --MacConkey--; and

UNITED STATES PATENT AND TRADEMARK OFFICE
CERTIFICATE OF CORRECTION

PATENT NO. : 4,929,466

DATED : May 29, 1990

INVENTOR(S) : Knutsson

It is certified that error appears in the above-identified patent and that said Letters Patent is hereby corrected as shown below:

Col. 5, line 40, "nate hydrogen" should read --nate-hydrogen--.

Signed and Sealed this

Thirty-first Day of December, 1991

*Attest:*

HARRY F. MANBECK, JR.

*Attesting Officer*      *Commissioner of Patents and Trademarks*